United States Patent [19]
Li

[11] Patent Number: 5,928,890
[45] Date of Patent: Jul. 27, 1999

[54] HUMAN AMINE RECEPTOR

[75] Inventor: Yi Li, Gaithersburg, Md.

[73] Assignee: Human Genome Sciences, Inc., Rockville, Md.

[21] Appl. No.: 08/467,559

[22] Filed: Jun. 6, 1995

[51] Int. Cl.$^6$ ................................................. C12N 15/12
[52] U.S. Cl. ................. 435/69.1; 435/252.3; 435/320.1; 435/325; 435/365; 536/23.5
[58] Field of Search ........................ 536/23.5; 435/69.1, 435/252.3, 320.1, 325, 365

[56] References Cited

PUBLICATIONS

Bunzow, J.R. et al., "Cloning and expression of a rat $D_2$ dopamine receptor cDNA," *Nature* 336:783–787 (1988).
Eva, C. et al., "Molecular cloning of a novel G protein–coupled that may belong to the neuropeptide receptor family," *FEBS Letts.* 271(1.2):81–84 (1990).
Hla, T. and T. Maciag, "An Abundant Transcript Induced in Differentiating Human Endothelial Cells Encodes a Polypeptide with Structural Similarities to G–protein–coupled Receptors," *J. Biol. Chem.* 265(16):9308–9313 (1990).
Johnson, G.L. and N. Dhanasekaran, "The G–Protein Family and Their Interaction with Receptors," *Endocrine Rev.* 10(3):317–331 (1989).
Kobilka, B.K. et al., "cDNA for the human $\beta_2$–adrenergic receptor: A protein with multiple membrane–spanning domains and encoded by a gene whose chromosomal location is shared with that of the receptor for platelet–derived growth factor," *Proc. Natl. Acad. Sci. USA* 84:46–50 (1987).

Kobilka, B.K. et al., "Cloning, Sequencing, and Expression of the Gene Coding for the Human Platelet $\alpha_2$–Adrenergic Receptor," *Science* 238:650–656 (1987).
Lefkowitz, R.J., "Thrombin Receptor: Variations on a theme," *Nature* 351:353–354 (1991).
Libert, F. et al., "Selective Amplification and Cloning of Four New Members on the G Protein–Coupled Receptor Family," *Science* 244:569–572 (1989).
Meyerhoff, W. et al., "Molecular cloning of a novel putative G–protein coupled receptor expressed during rat spermatogenesis," *FEBS Letts.* 284(2):155–160 (1991).
Ross, P.C. et al., "RTA, a candidate G protein–coupled receptor: Cloning, sequencing, and tissue distribution," *Proc. Natl. Acad. Sci. USA* 87:3052–3056 (1990).
Simon, M.I. et al., "Diversity of G Proteins in Signal Transduction," *Science* 252:802–808 (1991).
International Search Report for Application No. PCT/US95/07221.

*Primary Examiner*—David Saunders
*Attorney, Agent, or Firm*—Sterne, Kessler, Goldstein & Fox P.L.L.C.

[57] ABSTRACT

A Human amine receptor polypeptide and DNA (RNA) encoding such polypeptide and a procedure for producing such polypeptide by recombinant techniques is disclosed. Also provided are methods for detecting compounds which bind to and activate and bind to and inhibit such polypeptide and the use of compounds for treating diseases related to the under-expression and over-expression of the Human amine receptor of the present invention. Also disclosed are methods for detecting mutations in the nucleic acid sequence encoding the polypeptide and for detecting altered levels of the soluble form of the polypeptide.

25 Claims, 3 Drawing Sheets

FIG. 1

```
  3    AVFIQGAEEHPAAFCYQVNGSCPRTVH.TLGIQLVIYLTCAAGMLIIVLG     51
       | ::  |.... : :. . :||.| . : | |:.|:: |.    :|:||:|
 30    ARLLVLASPPASLLPPASEGSAPLSQQWTAGMGLLVALI....VLLIVVG     75

52    NVFVAFAVSYFKALHTPTNFLLLSLALADMFLGLLVLPLSTIRSVESCWF    101
       ||:| .|:.   . |:| ||::::||| ||::.||||:|:::..  |:|
 76    NVLVIVAIAKTPRLQTLTNLFIMSLASADLVMGLLVVPFGATIVVWGRWE    125

102    FGDFLCRLHTYLDTLFCLTSIFHLCFISIDRHCAICDPLLYPSKFTVRVA    151
       :|.|:| | | :|.| ..|| ||.|.:||. ||..|: |.| :|    |
126    YGSFFCELWTSVDVLCVTASIETLCVIALDRYLAITSPFRYQSLLTRARA    175

152    LRYILAGWGVPAAYTSLFLYTDVVETRLSQWLEEMPCVG...SCQLLLNK    198
        .:  ..|::.|    : :.. ::. :  ...  |...|  .  :|:::|:
176    RALVCTVWAISAL...VSFLPILMHWWRAESDEARRCYNDPKCCDFVTNR    222

199    FWGWLNFPL.FFVPCLIMISLYVKIFVVATRQAQQITTLSKSLAGA....    243
       ::   . .: |:||  ||  :|:::|  |  :|...|..  .:: |:
223    AYAIASSVVSFYVPLCIMAFVYLRVFREAQKQVKKIDSCERRFLGGPARP    272

244    ............................AKHERKAAKTLGIVVGIY       261
                                   | :|.|| |||||::|::
273    PSPEPSPSPGPPRPADSLANGRSSKRRPSRLVALREQKALKTLGIIMGVF    322

262    LLCWLPFTIDTMVDSLLHFITPPLVFDIFIWFAYFNSACNPIIYVFSYQW    311
       ||||||  :..:|..: : :.|. :| :| |::| ||| |||||. | ::
323    TLCWLPFFLANVVKAFHRDLVPDRLFVFFNWLGYANSAFNPIIYCRSPDF    372

312    FRKALKLTLSQKVFSPQTRTVD      333
        :   :|  :.:  ... |...
373    RKAFQRLLCCARRAACRRRAAH      394
```

FIG.2

```
  8  GAEEHPAAFCYQVNGSCPRTVHTLGIQLVIYLTCAAGMLIIVLGNVFVAF   57
     ..: ........::..|||..:. :.    ....||    ::||:|||:|.:
 10  DDDLERQNWSRPFNGSDGKADRPHYNYYATLLT...LLIAVIVFGNVLVCM   57

58  AVSYFKALHTPTNFLLLSLALADMFLGLLVLPLSTIRSVESCWFFGDFLC   107
     |||   |||:|.||:|:::|||:||::::  ||:|:  ..  |:  || :  :  |
 58  AVSREKALQTTTNYLIVSLAVADLLVATLVMPWVVYLEVVGEWKFSRIHC   107

108  RLHTYLDTLFCLTSIFHLCFISIDRHCAICDPLLYPSKFTVRVALRYILA   157
     : . ||.::| .||::|| ||||| ..|:. |:||  .::. :  : :::.
108  DIFVTLDVMMCTASILNLCAISIDRYTAVAMPMLYNTRYSSKRRVTVMIS   157

158  .GWGVPAAYTSLFLYTDVVETRLSQWLEEMPCVGSCQLLLNKFWGWLNFP   206
     .|.:. ...: :|:.      |..  :: ..:::..:::      :  .:.
158  IVWVLSFTISCPLLFG......LNNADQNECIIANPAFVV.....YSSIV   196

207  LFFVPCLIMISLYVKIFVVATRQAQQITT..........LSKSLAGAAKH   246
     |:|| :: : :|:||::| |.  ...|            |. .| :||::
197  SFYVPFIVTLLVYIKIYIVLRRRRKRVNTKRSSRAFRAHLRAPLKEAARR   246

247  ..................................ERKAAKTL         254
                                        |:||.. |
297  EKNGHAKDHPKIAKIFEIQTMPNGKTRTSLKTMSRRKLSQQKEKKATQML   346

255  GIVVGIYLLCWLPFTIDTMVDSLLHFITPPLVFDIFIWFAYFNSACNPII   304
     :||:|::::|||||  |.  :::     .||:::. |.|::|.|||.||||
347  AIVLGVFIICWLPFFITHILNIHCDCNIPPVLYSAFTWLGYVNSAVNPII   396

305  YVFSYQWFRKALKLTL   320
     |.      ||||:  .|
397  YTTFNIEFRKAFLKIL   412
```

FIG.3 ns,890

HUMAN AMINE RECEPTOR

This invention relates to newly identified polynucleotides, polypeptides encoded by such polynucleotides, the use of such polynucleotides and polypeptides, as well as the production of such polynucleotides and polypeptides. More particularly, the polypeptide of the present invention are human 7-transmembrane receptors and has been putatively identified as a human amine receptor. The invention also relates to inhibiting the action of such polypeptides.

It is well established that many medically significant biological processes are mediated by proteins participating in signal transduction pathways that involve G-proteins and/or second messengers, e.g., CAMP (Lefkowitz, Nature, 351:353–354 (1991)). Herein these proteins are referred to as proteins participating in pathways with G-proteins or PPG proteins. Some examples of these proteins include the GPC receptors, such as those for adrenergic agents and dopamine (Kobilka, B. K., et al., PNAS, 84:46–50 (1987); Kobilka, B. K., et al., Science, 238:650–656 (1987); Bunzow, J. R., et al., Nature, 336:783–787 (1988)), G-proteins themselves, effector proteins, e.g., phospholipase C, adenyl cyclase, and phosphodiesterase, and actuator proteins, e.g., protein kinase A and protein kinase C (Simon, M. I., et al., Science, 252:802–8 (1991)).

For example, in one form of signal transduction, the effect of hormone binding is activation of an enzyme, adenylate cyclase, inside the cell. Enzyme activation by hormones is dependent on the presence of the nucleotide GTP, and GTP also influences hormone binding. A G-protein connects the hormone receptors to adenylate cyclase. G-protein was shown to exchange GTP for bound GDP when activated by hormone receptors. The GTP-carrying form then binds to an activated adenylate cyclase. Hydrolysis of GTP to GDP, catalyzed by the G-protein itself, returns the G-protein to its basal, inactive form. Thus, the G-protein serves a dual role, as an intermediate that relays the signal from receptor to effector, and as a clock that controls the duration of the signal.

The membrane protein gene superfamily of G-protein coupled receptors has been characterized as having seven putative transmembrane domains. The domains are believed to represent transmembrane α-helices connected by extracellular or cytoplasmic loops. G-protein coupled receptors include a wide range of biologically active receptors, such as hormone, viral, growth factor and neuroreceptors.

G-protein coupled receptors can be intracellularly coupled by heterotrimeric G-proteins to various intracellular enzymes, ion channels and transporters (see, Johnson et al., Endoc., Rev., 10:317–331 (1989)). Different G-protein α-subunits preferentially stimulate particular effectors to modulate various biological functions in a cell. Phosphorylation of cytoplasmic residues of G-protein coupled receptors have been identified as an important mechanism for the regulation of G-protein coupling of some G-protein coupled receptors. G-protein coupled receptors are found in numerous sites within a mammalian host.

The Human Amine Receptor of the present invention is a G-protein coupled receptor. Neurosensory and neuromotor functions are carried out by neurotransmission. Neurotransmission is the conductance of a nerve impulse from one neuron, called the presynaptic neuron, to another neuron, called the postsynaptic neuron, across the synaptic cleft. Transmission of the nerve impulse across the synaptic cleft involves the secretion of neurotransmitter substances. The neurotransmitter is packaged into vesicles in the presynaptic neuron and released into the synaptic cleft to find its receptor at the postsynaptic neuron. Transmission of the nerve impulse is normally transient.

An essential property of synaptic transmission is the rapid termination of action following neurotransmitter release. For many neurotransmitters, including catecholamine, serotonin, and certain amino acids (e.g., gamma-aminobutyric acid (GABA), glutamate and glycine), rapid termination of synaptic action is achieved by the uptake of the neurotransmitter into the presynaptic terminal and surrounding glial cells. This rapid re-accumulation of a neurotransmitter is the result of re-uptake by the presynaptic terminals.

At presynaptic terminals, the various molecular structures for re-uptake are highly specific for such neurotransmitters as choline and the biogenic amines (low molecular weight neurotransmitter substances such as dopamine, norepinephrine, epinephrine, serotonin and histamine). These molecular apparatuses are receptors which are termed transporters. These transporters move neurotransmitter substances from the synaptic cleft back across the cell membrane of the presynaptic neuron into the cytoplasm of the presynaptic terminus and therefore terminate the function of these substances. Inhibition or stimulation of neurotransmitter uptake provides a means for modulating the effects of the endogenous neurotransmitters.

The neurotransmitter substances are implicated in numerous pathophysiologies and treatments including, movement disorders, schizophrenia, drug addiction, anxiety, migraine headaches, epilepsy, myoclonus, spastic paralysis, muscle spasm, schizophrenia, cognitive impairment, depression, Parkinson's Disease and Alzheimer's Disease, among others.

Re-uptake of neurotransmitter substances by the transporters may be sodium-dependent. For instance, the GABA transporter is a member of the recently described sodium-dependent neurotransmitter transporter gene family. These transporters are transmembrane receptor complexes having an extracellular portion, a transmembrane portion and an intracellular portion. A significant degree of homology exists in the transmembrane domains of the entire family of sodium-dependent neurotransmitter transporter proteins, with considerable stretches of identical amino acids, while much less homology is apparent in the intracellular and extracellular loops connecting these domains. The extracellular loop in particular seems to be unique for each transporter. This region may contribute to substrate and/or inhibitor specificities.

The polypeptide of the present invention has been putatively identified as an amine receptor. This identification has been made as a result of amino acid sequence homology to the rat amine receptor.

In accordance with one aspect of the present invention, there are provided novel mature receptor polypeptides as well as biologically active and diagnostically or therapeutically useful fragments, analogs and derivatives thereof. The receptor polypeptides of the present invention are of human origin.

In accordance with another aspect of the present invention, there are provided isolated nucleic acid molecules encoding the receptor polypeptides of the present invention, including mRNAs, DNAs, cDNAs, genomic DNA as well as antisense analogs thereof and biologically active and diagnostically or therapeutically useful fragments thereof.

In accordance with a further aspect of the present invention, there are provided processes for producing such receptor polypeptides by recombinant techniques comprising culturing recombinant prokaryotic and/or eukaryotic host cells, containing nucleic acid sequences encoding the receptor polypeptides of the present invention, under conditions promoting expression of said polypeptides and subsequent recovery of said polypeptides.

In accordance with yet a further aspect of the present invention, there are provided antibodies against such receptor polypeptides.

In accordance with another aspect of the present invention there are provided methods of screening for compounds which bind to and activate or inhibit activation of the receptor polypeptides of the present invention.

In accordance with still another embodiment of the present invention there are provided processes of administering compounds to a host which bind to and activate the receptor polypeptide of the present invention for the prevention and/or treatment of abnormal conditions resulting from under-expression of the amino receptor of the present invention.

In accordance with another aspect of the present invention there is provided a method of administering the receptor polypeptides of the present invention via gene therapy to treat conditions related to under-expression of the polypeptide or underexpression of a ligand to the receptor polypeptide.

In accordance with still another embodiment of the present invention there are provided processes of administering compounds which bind to and inhibit activation of the receptor polypeptides of the present invention for prevention and/or treatment of conditions resulting from expression of the amine receptor of the present invention.

In accordance with yet another aspect of the present invention, there are provided nucleic acid probes comprising nucleic acid molecules of sufficient length to specifically hybridize to the polynucleotide sequences of the present invention.

In accordance with still another aspect of the present invention, there are provided diagnostic assays for detecting diseases related to mutations in the nucleic acid sequences encoding such polypeptides and for detecting an altered level of the soluble form of the receptor polypeptides.

In accordance with yet a further aspect of the present invention, there are provided processes for utilizing such receptor polypeptides, or polynucleotides encoding such polypeptides, for in vitro purposes related to scientific research, synthesis of DNA and manufacture of DNA vectors.

These and other aspects of the present invention should be apparent to those skilled in the art from the teachings herein.

The following drawings are illustrative of embodiments of the invention and are not meant to limit the scope of the invention as encompassed by the claims.

FIG. 1 illustrates the cDNA sequence (SEQ ID NO:1) and corresponding deduced amino acid sequence (SEQ ID NO:2) of the human amine receptor of the present invention. The standard one-letter abbreviations for amino acids are used. Sequencing was performed using a 373 Automated DNA sequencer (Applied Biosystems, Inc.).

FIG. 2 is an illustration of an amino acid homology alignment between the amine transporter or the present invention (SEQ ID NO:2) (top line) and murine β-1 Adrenoreceptor (SEQ ID NO:9) (bottom line).

FIG. 3 is an illustration of an amino acid homology alignment between the amine transporter or the present invention (SEQ ID NO:2) (top line) and human dopamine D2 receptor (SEQ ID NO:10) (bottom line).

The amine receptor of the present invention may be responsible for re-uptake of one or any of the amine neurotransmitters present in mammalian cells. Examples of such amine transporters include, but are not limited to, dopamine, norepinephrine, epinephrine, serotonin and histamine, and other amino acid transmitters, including GABA, glycine and glutamate.

Figure 1:
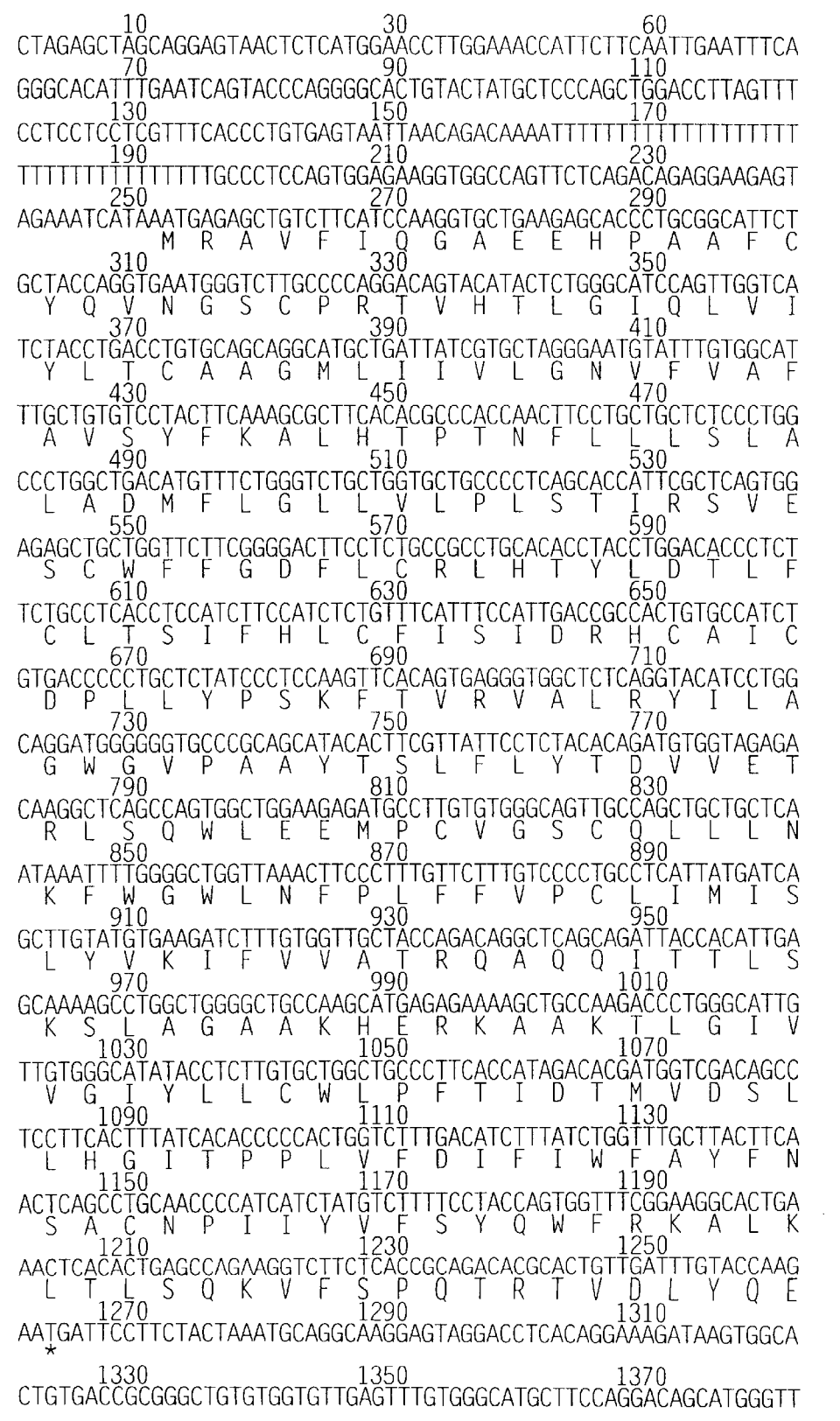

In accordance with an aspect of the present invention, there is provided an isolated nucleic acid (polynucleotide) which encodes for the mature polypeptide having the deduced amino acid sequence of FIG. 1 (SEQ ID NO:2) or for the mature polypeptide encoded by the cDNA of the clone deposited as ATCC Deposit No. 97181 on Jun. 1, 1995 at the American Type Culture Collection, 10801 University Boulevard, Manassas Va. 20110-2209.

A polynucleotide encoding a polypeptide of the present invention may be found in human monocytes. The polynucleotide of this invention was discovered in a human genomic library. It is structurally related to the G protein-coupled receptor family. It contains an open reading frame encoding a protein of 337 amino acid residues. The protein exhibits the highest degree of homology to a murine β-1 Adrenoreceptor with 32.099% identity and 55.864% similarity over a 330 amino acid stretch. The protein also exhibits homology to a human dopamine $D_2$ receptor with 32% identity and 58.333% similarity over a 312 amino acid stretch.

The polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in FIG. 1 (SEQ ID NO:1) or that of the deposited clone or may be a different coding sequence which coding sequence, as a result of the redundancy or degeneracy of the genetic code, encodes the same mature polypeptide as the DNA of FIG. 1 (SEQ ID NO:1) or the deposited cDNA.

The polynucleotide which encodes for the mature polypeptide of FIG. 1 (SEQ ID NO:2) or for the mature polypeptide encoded by the deposited cDNA may include: only the coding sequence for the mature polypeptide; the coding sequence for the mature polypeptide and additional coding sequence; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the deduced amino acid sequence of FIG. 1 (SEQ ID NO:2) or the polypeptide encoded by the cDNA of the deposited clone. The variant of the polynucleotide may be a naturally occurring allelic variant of the polynucleotide or a non-naturally occurring variant of the polynucleotide.

Thus, the present invention includes polynucleotides encoding the same mature polypeptide as shown in FIG. 1 (SEQ ID NO:2) or the same mature polypeptide encoded by the cDNA of the deposited clone as well as variants of such polynucleotides which variants encode for a fragment, derivative or analog of the polypeptide of FIG. 1 (SEQ ID NO:2) or the polypeptide encoded by the cDNA of the deposited clone. Such nucleotide variants include deletion variants, substitution variants and addition or insertion variants.

As hereinabove indicated, the polynucleotide may have a coding sequence which is a naturally occurring allelic variant of the coding sequence shown in FIG. 1 (SEQ ID No:1) or of the coding sequence of the deposited clone. As known in the art, an allelic variant is an alternate form of a polynucleotide sequence which may have a substitution, deletion or addition of one or more nucleotides, which does not substantially alter the function of the encoded polypeptide.

The polynucleotides may also encode for a soluble form of the amine receptor polypeptide which is the extracellular portion of the polypeptide which has been cleaved from the TM and intracellular domain of the full-length polypeptide of the present invention.

The polynucleotides of the present invention may also have the coding sequence fused in frame to a marker sequence which allows for purification of the polypeptide of the present invention. The marker sequence may be a hexahistidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

Fragments of the full length gene of the present invention may be used as a hybridization probe for a cDNA library to isolate the full length cDNA and to isolate other cDNAs which have a high sequence similarity to the gene or similar biological activity. Probes of this type preferably have at least 30 bases and may contain, for example, 50 or more bases. The probe may also be used to identify a cDNA clone corresponding to a full length transcript and a genomic clone or clones that contain the complete gene including regulatory and promotor regions, exons, and introns. An example of a screen comprises isolating the coding region of the gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

The present invention further relates to polynucleotides which hybridize to the hereinabove-described sequences if there is at least 70%, preferably at least 90%, and, more preferably at least 95% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which either retain substantially the same biological function or activity as the mature polypeptide encoded by the cDNAs of FIG. 1 (SEQ ID NO:1) or the deposited cDNA(s), i.e. function as a soluble amine receptor by retaining the ability to bind the ligands for the receptor even though the polypeptide does not function as a membrane bound amine receptor, for example, by eliciting a second messenger response.

Alternatively, the polynucleotides may have at least 20 bases, preferably 30 bases and more preferably at least 50 bases which hybridize to a polynucleotide of the present invention and which have an identity thereto, as hereinabove described, and which may or may not retain activity. Such polynucleotides may be employed as probes for the polynucleotide of SEQ ID NO: 1, or for variants thereof, for example, for recovery of the polynucleotide or as a diagnostic probe or as a PCR primer.

Thus, the present invention is directed to polynucleotides having at least a 70% identity, preferably at least 90% and more preferably at least a 95% identity to a polynucleotide which encodes the polypeptide of SEQ ID NO:2 as well as fragments thereof, which fragments have at least 30 bases and preferably at least 50 bases and to polypeptides encoded by such polynucleotides.

The deposit(s) referred to herein will be maintained under the terms of the Budapest Treaty on the International Recognition of the Deposit of Micro-organisms for purposes of Patent Procedure. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted.

The present invention further relates to a human amine receptor polypeptide which has the deduced amino acid sequence of FIG. 1 (SEQ ID No. 2) or which has the amino acid sequence encoded by the deposited cDNA, as well as fragments, analogs and derivatives of such polypeptide.

The terms "fragment," "derivative" and "analog" when referring to the polypeptide of FIG. 1 (SEQ ID No. 2) or that encoded by the deposited cDNA, means a polypeptide which retains essentially the same biological function or activity as such polypeptide, i.e. functions as an amine receptor, or retains the ability to bind the ligand for the receptor even though the polypeptide does not function as a G-protein coupled receptor, for example, a soluble form of the receptor.

The polypeptide of the present invention may be a recombinant polypeptide, a natural polypeptide or a synthetic polypeptide, preferably a recombinant polypeptide.

The fragment, derivative or analog of the polypeptide of FIG. 1 (SEQ ID No. 2) or that encoded by the deposited cDNA may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol) or (iv) one in which the additional amino acids are fused to the mature polypeptide which are employed for purification of the mature polypeptide or (v) one in which a fragment of the polypeptide is soluble, i.e. not membrane bound, yet still binds ligands to the membrane bound receptor. Such fragments, derivatives and analogs are deemed to be within the scope of those skilled in the art from the teachings herein.

The polypeptides and polynucleotides of the present invention are preferably provided in an isolated form, and preferably are purified to homogeneity.

The polypeptides of the present invention include the polypeptide of SEQ ID NO:2 (in particular the mature polypeptide) as well as polypeptides which have at least 70% similarity (preferably at least 70% identity) to the polypeptide of SEQ ID NO:2 and more preferably at least 90% similarity (more preferably at least 90% identity) to the polypeptide of SEQ ID NO:2 and still more preferably at least 95% similarity (still more preferably at least 95% identity) to the polypeptide of SEQ ID NO:2 and to portions of such polypeptide with such portion of the polypeptide generally contains at least 30 amino acids and more preferably at least 50 amino acids.

As known in the art "similarity" between two polypeptides is determined by comparing the amino acid sequence and conserved amino acid substitutes thereto of the polypeptide to the sequence of a second polypeptide.

Fragments or portions of the polypeptides of the present invention may be employed for producing the corresponding full-length polypeptide by peptide synthesis, therefore, the fragments may be employed as intermediates for producing the full-length polypeptides. Fragments or portions of the polynucleotides of the present invention may be used to synthesize full-length polynucleotides of the present invention.

The term "gene" means the segment of DNA involved in producing a polypeptide chain; it includes regions preceding and following the coding region "leader and trailer" as well as intervening sequences (introns) between individual coding segments (exons).

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polypeptides of the present invention include the polypeptide of SEQ ID NO:2 (in particular the mature polypeptide) as well as polypeptides which have at least 70% similarity (preferably at least 70% identity) to the polypeptide of SEQ ID NO:2 and more preferably at least 90% similarity (more preferably at least 90% identity) to the polypeptide of SEQ ID NO:2 and still more preferably at least 95% similarity (still more preferably at least 95% identity) to the polypeptide of SEQ ID NO:2 and also include portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the genes of the present invention. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence (s) (promoter) to direct mRNA synthesis. As representative examples of such promoters, there may be mentioned: LTR or SV40 promoter, the $E.$ $coli.$ lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in $E.$ $coli.$ The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as $E.$ $coli,$ Streptomyces, $Salmonella$ $typhimurium;$ fungal cells, such as yeast; insect cells such as Drosophila S2 and Spodoptera Sf9; animal cells such as CHO, HEK, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (Qiagen), pBS, pD10, phagescript, psiX174, pbluescript SK, pbsks, pNH8A, pNH16a, pNH18A, pNH46A (Stratagene); ptrc99a, pKK223-3, pKK233-3, pDR540, pRIT5 (Pharmacia). Eukaryotic: pWLNEO, pSV2CAT, pOG44, pXT1, pSG (Stratagene) pSVK3, pBPV, PMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are PKK232-8 and PCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DRAE-Dextran mediated transfection, or electroporation (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of E. coli and S. cerevisiae TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include E. coli, Bacillus subtilis, Salmonella typhimurium and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HEK, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking non-transcribed sequences. DNA sequences derived from the SV40 splice, and polyadenylation sites may be used to provide the required nontranscribed genetic elements.

The human amine receptor polypeptide can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture).

Depending upon the host employed in a recombinant production procedure, the polypeptides of the present invention may be glycosylated or may be non-glycosylated. Polypeptides of the invention may also include an initial methionine amino acid residue.

Fragments of the full length human amine transporter gene may be used as a hybridization probe for a CDNA library to isolate the full length gene and to isolate other genes which have a high sequence similarity to the gene or similar biological activity. Probes of this type are at least 20 bases, preferably at least 30 bases and most preferably at least 50 bases or more. The probe may also be used to identify a CDNA clone corresponding to a full length transcript and a genomic clone or clones that contain the complete human amine transporter gene including regulatory and promotor regions, exons, and introns. As an example of a screen comprises isolating the coding region of the human amine transporter gene by using the known DNA sequence to synthesize an oligonucleotide probe. Labeled oligonucleotides having a sequence complementary to that of the gene of the present invention are used to screen a library of human CDNA, genomic DNA or mRNA to determine which members of the library the probe hybridizes to.

This invention provides a method for determining amine neurotransmitters which are transported by the human amine receptor of the present invention. An example of an assay which will identify these neurotransmitters comprises infecting mammalian cells with recombinant vaccinia virus strain VTF-7 encoding a T7 RNA polymerase and following such infection with liposome-mediated transfection with the amine receptor gene of the present invention through the use of a vector, for example, pBSSKII(−). Controlled transfections are also done with equivalent amounts of vector alone. Assays are performed eight hours following transfection in modified Krebs-Ringer-HEPES buffer. Cells are then incubated with [$^3$H] neurotransmitter (for example, GABA, dopamine, serotonin, etc.). Uptake is stopped by placing the cells on ice. Cells are solubilized in one percent SDS, and the amount of radioactivity accumulated is determined by liquid scintillation counting. A significant amount of uptake determines that the particular neurotransmitter is taken up by the human amine receptor of the present invention by determining background using control transfections with pBSSKII for each assay and subtracting the values obtained from the signals determined for the specific amine neurotransmitters.

This invention also provides a method of detecting expression of the amine receptor of the present invention on the surface of a cell by detecting the presence of mRNA coding for the amine receptor. This method comprises obtaining total mRNA from the cell using methods well-known in the art and contacting the mRNA so obtained with a nucleic acid probe of at least 10 nucleotides and which is capable of specifically hybridizing with a sequence included within the sequence of a nucleic acid molecule encoding a human amine receptor of the present invention under hybridizing conditions, detecting the presence of mRNA hybridized to the probe, and thereby detecting the expression of the amine receptor by the cell. Hybridization of probes to target nucleic acid molecules such as mRNA molecules employs techniques well known in the art. However, in one embodiment of this invention, nucleic acids are extracted by precipitation from lysed cells and the mRNA is isolated from the extract using a column which binds the poly-A tails of the mRNA molecules. The mRNA is then exposed to radioactively labelled probe on a nitrocellulose membrane, and the probe hybridizes to and thereby labels complementary mRNA sequences. Binding may be detected by autoradiography or scintillation counting. However, other methods for performing these steps are well known to those of skill in the art.

Alternatively, an antibody directed to the human amine receptor may be employed under conditions permitting binding of the antibody to the transporter, and detecting the presence of the receptor on the surface of the cell. Such a method may be employed for determining whether a given cell is defective in expression of the amine receptor. Detection methods include fluorescent markers bound to the antibodies.

The invention also provides a method for determining whether a compound not known to be capable of specifically binding to a human amine receptor can specifically bind to the human amine receptor, which comprises contacting a mammalian cell comprising a plasmid adapted for expression in a mammalian cell which plasmid further comprises a DNA which expresses the amine receptor on the cell surface with the compound under conditions permitting binding of ligands known to bind to the amine receptor, detecting the presence of any compound bound to the amine receptor, the presence of bound compound indicating that the compound is capable of specifically binding to the human amine receptor.

The polynucleotides and polypeptides of the present invention may be employed as research reagents and materials for discovery of treatments and diagnostics to human disease.

The amine receptor of the present invention may be employed in a process for screening for compounds which activate (agonists) or inhibit activation (antagonists) of the receptor polypeptide of the present invention .

In general, such screening procedures involve providing appropriate cells which express the receptor polypeptide of the present invention on the surface thereof. Such cells include cells from mammals, yeast, drosophila or E. Coli. In particular, a polynucleotide encoding the receptor of the present invention is employed to transfect cells to thereby express the amine receptor. The expressed receptor is then contacted with a test compound to observe binding, stimulation or inhibition of a functional response.

One such screening procedure involves the use of melanophores which are transfected to express the amine receptor of the present invention. Such a screening technique is described in PCT WO 92/01810 published Feb. 6, 1992.

Thus, for example, such assay may be employed for screening for a compound which inhibits activation of the receptor polypeptide of the present invention by contacting the melanophore cells which encode the receptor with both the receptor ligand and a compound to be screened. Inhibition of the signal generated by the ligand indicates that a compound is a potential antagonist for the receptor, i.e., inhibits activation of the receptor.

The screen may be employed for determining a compound which activates the receptor by contacting such cells with compounds to be screened and determining whether such compound generates a signal, i.e., activates the receptor.

Other screening techniques include the use of cells which express the amine receptor (for example, transfected CHO cells) in a system which measures extracellular pH changes caused by receptor activation, for example, as described in Science, volume 246, pages 181–296 (October 1989). For example, compounds may be contacted with a cell which expresses the receptor polypeptide of the present invention and a second messenger response, e.g. signal transduction or pH changes, may be measured to determine whether the potential compound activates or inhibits the receptor.

Another such screening technique involves introducing RNA encoding the amine receptor into Xenopus oocytes to transiently express the receptor. The receptor oocytes may then be contacted with the receptor ligand and a compound to be screened, followed by detection of inhibition or activation of a calcium signal in the case of screening for compounds which are thought to inhibit activation of the receptor.

Another screening technique involves expressing the amine receptor in which the receptor is linked to a phospholipase C or D. As representative examples of such cells, there may be mentioned endothelial cells, smooth muscle cells, embryonic kidney cells, etc. The screening may be accomplished as hereinabove described by detecting activation of the receptor or inhibition of activation of the receptor from the phospholipase second signal.

Another method involves screening for compounds which inhibit activation of the receptor polypeptide of the present invention antagonists by determining inhibition of binding of labeled ligand to cells which have the receptor on the surface thereof. Such a method involves transfecting a eukaryotic cell with DNA encoding the amine receptor such that the cell expresses the receptor on its surface and contacting the cell with a compound in the presence of a labeled form of a known ligand. The ligand can be labeled, e.g., by radioactivity. The amount of labeled ligand bound to the receptors is measured, e.g., by measuring radioactivity of the receptors. If the compound binds to the receptor as determined by a reduction of labeled ligand which binds to the receptors, the binding of labeled ligand to the receptor is inhibited.

Amine receptors are ubiquitous in the mammalian host and are responsible for many biological functions, including many pathologies. Accordingly, it is desirous to find compounds and drugs which stimulate the amine receptor on the one hand and which can inhibit the function of a amine receptor on the other hand.

Examples of compounds which bind to and inhibit the amine receptor of the present invention includes antibodies, or in some cases an oligopeptides, which bind to the amine receptor but do not elicit a second messenger response such that the activity of the amine receptor is prevented. Antibodies include anti-idiotypic antibodies which recognize unique determinants generally associated with the antigen-binding site of an antibody.

Another example includes proteins which are closely related to the ligand of the amine receptors, i.e. a fragment of the ligand, which has lost biological function and when binding to the amine receptor, elicits no response.

An antisense construct prepared through the use of antisense technology, may be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix—see Lee et al., Nucl. Acids Res., 6:3073 (1979); Cooney et al, Science, 241:456 (1988); and Dervan et al., Science, 251: 1360 (1991)), thereby preventing transcription and the production of the amine receptor. The antisense RNA oligonucleotide hybridizes to the mRNA in vivo and blocks translation of mRNA molecules into amine receptor (antisense—Okano, J. Neurochem., 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of the amine receptor.

A small molecule which binds to the amine receptor, making it inaccessible to ligands such that normal biological activity is prevented, for example small peptides or peptide-like molecules, may also be used to inhibit activation of the receptor polypeptide of the present invention.

A soluble form of the amine receptor, e.g. a fragment of the receptor, may be used to inhibit activation of the receptor by binding to the ligand to the receptor polypeptide of the present invention and preventing the ligand from interacting with membrane bound amine receptors.

This invention additionally provides a method of treating an abnormal condition related to expression of the amine receptor of the present invention which comprises administering to a subject an inhibitory compound as hereinabove described along with a pharmaceutically acceptable carrier in an amount effective to block bind to a human amine receptor can specifically bind to the human amine receptor, which comprises contacting a mammalian cell comprising a plasmid adapted for expression in a mammalian cell which plasmid further comprises a DNA which expresses the amine receptor on the cell surface with the compound under conditions permitting binding of ligands known to bind to the amine receptor, detecting the presence of any compound bound to the amine receptor, the presence of bound compound indicating that the compound is capable of specifically binding to the human amine receptor.

The polynucleotides and polypeptides of the present invention may be employed as research reagents and materials for discovery of treatments and diagnostics to human disease.

The amine receptor of the present invention may be employed in a process for screening for compounds which activate (agonists) or inhibit activation (antagonists) of the receptor polypeptide of the present invention.

In general, such screening procedures involve providing appropriate cells which express the receptor polypeptide of the present invention on the surface thereof. Such cells include cells from mammals, yeast, drosophila or E. Coli. In particular, a polynucleotide encoding the receptor of the present invention is employed to transfect cells to thereby express the amine receptor. The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the pharmaceutical compositions may be employed in conjunction with other therapeutic compounds.

The pharmaceutical compositions may be administered in a convenient manner such as by the oral, topical, intravenous, intraperitoneal, intramuscular, subcutaneous, intranasal or intradermal routes. The pharmaceutical compositions are administered in an amount which is effective for treating and/or prophylaxis of the specific indication. In general, they are administered in an amount of at least about 10 $\mu$g/kg body weight and in most cases they will be administered in an amount not in excess of about 8 mg/Kg body weight per day. In most cases, the dosage is from about 10 μg/kg to about 1 mg/kg body weight daily, taking into account the routes of administration, symptoms, etc.

The human amine receptor and agonist and antagonist compounds which are polypeptides may also be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art. For example, cells may be engineered by procedures known in the art by use of a retroviral particle containing RNA encoding a polypeptide of the present invention.

Similarly, cells may be engineered in vivo for expression of a polypeptide in vivo by, for example, procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a polypeptide of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

The vector includes one or more promoters. Suitable promoters which may be employed include, but are not limited to, the retroviral LTR; the SV40 promoter; and the human cytomegalovirus (CMV) promoter described in Miller, et al., *Biotechniques*, Vol. 7, No. 9, 980–990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or hetorologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the β-actin promoter; and human growth hormone promoters. The promoter also may be the native promoter which controls the genes encoding the polypeptides.

The retroviral plasmid vector is employed to transduce packaging cell lines to form producer cell lines. Examples of packaging cells which may be transfected include, but are not limited to, the PE501, PA317, ψ-2, ψ-AM, PA12, T19-14X, VT-19-17-H2, ψCRE, ψCRIP, GP+E-86, GP+envAm12, and DAN cell lines as described in Miller, *Human Gene Therapy*, Vol. 1, pgs. 5–14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

This invention is also related to the use of the human amine receptor gene as part of a diagnostic assay for detecting diseases or susceptibility to diseases related to the presence of mutations in the human amine receptor genes. Such diseases are related to under-expression of the human amine receptor.

Individuals carrying mutations in the human amine receptor gene may be detected at the DNA level by a variety of techniques. Nucleic acids for diagnosis may be obtained from a patient's cells, such as from blood, urine, saliva, tissue biopsy and autopsy material. The genomic DNA may be used directly for detection or may be amplified enzymatically by using PCR (Saiki et al., Nature, 324:163–166 (1986)) prior to analysis. RNA or cDNA may also be used for the same purpose. As an example, PCR primers complementary to the nucleic acid encoding the human amine receptor protein can be used to identify and analyze human amine receptor mutations. For example, deletions and insertions can be detected by a change in size of the amplified product in comparison to the normal genotype. Point mutations can be identified by hybridizing amplified DNA to radiolabeled human amine receptor RNA or alternatively, radiolabeled human amine receptor antisense DNA sequences. Perfectly matched sequences can be distinguished from mismatched duplexes by RNase A digestion or by differences in melting temperatures.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., Science, 230:1242 (1985)).

Sequence changes at specific locations may also be revealed by nuclease protection assays, such as RNase and S1 protection or the chemical cleavage method (e.g., Cotton et al., PNAS, USA, 85:4397–4401 (1985)).

Thus, the detection of a specific DNA sequence may be achieved by methods such as hybridization, RNase protection, chemical cleavage, direct DNA sequencing or the use of restriction enzymes, (e.g., Restriction Fragment Length Polymorphisms (RFLP)) and Southern blotting of genomic DNA.

In addition to more conventional gel-electrophoresis and DNA sequencing, mutations can also be detected by in situ analysis.

The present invention also relates to a diagnostic assay for detecting altered levels of soluble forms of the amine receptor polypeptides of the present invention in various tissues which may be employed to diagnose diseases related to under-expression of the amine receptor. Assays used to detect levels of the soluble receptor polypeptides in a sample derived from a host are well known to those of skill in the art and include radioimmunoassays, competitive-binding assays, Western blot analysis and preferably as ELISA assay.

An ELISA assay initially comprises preparing an antibody specific to antigens of the amine receptor polypeptides, preferably a monoclonal antibody. In addition a reporter antibody is prepared against the monoclonal antibody. To the reporter antibody is attached a detectable reagent such as radioactivity, fluorescence or in this example a horseradish peroxidase enzyme. A sample is now removed from a host and incubated on a solid support, e.g. a polystyrene dish, that binds the proteins in the sample. Any free protein binding sites on the dish are then covered by incubating with a non-specific protein such as bovine serum albumin. Next, the monoclonal antibody is incubated in the dish during which time the monoclonal antibodies attach to any amine receptor proteins attached to the polystyrene dish. All unbound monoclonal antibody is washed out with buffer. The reporter antibody linked to horseradish peroxidase is now placed in the dish resulting in binding of the reporter antibody to any monoclonal antibody bound to amine receptor proteins. Unattached reporter antibody is then washed out. Peroxidase substrates are then added to the dish and the amount of color developed in a given time period is a measurement of the amount of amine receptor proteins present in a given volume of patient sample when compared against a standard curve.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the 3' untranslated region is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA as short as 50 or 60 bases. For a review of this technique, see Verma et al., Human Chromosomes: a Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 μg of plasmid or DNA fragment is used with about 2 units of enzyme in about 20 μl of buffer solution. For the purpose of isolating DNA fragments for plasmid construction, typically 5 to 50 μg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980). "Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units of T4 DNA ligase ("ligase") per 0.5 μg of approximately equimolar amounts of the DNA fragments to be ligated.

Unless otherwise stated, transformation was performed as described in the method of Graham, F. and Van der Eb, A., Virology, 52:456–457 (1973).

EXAMPLE 1

Bacterial Expression and Purification of Human Amine Receptor

The DNA sequence encoding human amine receptor, ATCC # 97181, is initially amplified using PCR oligonucleotide primers corresponding to the 5' and 3' end sequences of the processed amine receptor nucleic acid sequence (minus the signal peptide sequence). Additional nucleotides corresponding to amine receptor gene are added to the 5' and 3' sequences respectively. The 5' oligonucleotide primer has the sequence 5' CGGAATTCCTUATGAGAGCTGTCT-TCATC 3' (SEQ ID.No. 3) contains an EcoRI restriction enzyme site followed by 18 nucleotides of human amine receptor coding sequence starting from the presumed terminal amino acid of the processed protein. The 3' sequence 5' CGGAAGCTTCGTCATTCTTGGTACAAATCAAC 3' (SEQ ID No. 4) contains complementary sequences to an HindIII site and is followed by 18 nucleotides of the human amine receptor gene. The restriction enzyme sites correspond to the restriction enzyme sites on the bacterial expression vector pQE-9 (Qiagen, Inc. Chatsworth, Calif.). pQE-9 encodes antibiotic resistance (Ampr), a bacterial origin of replication (ori), an IPTG-regulatable promoter operator (P/O), a ribosome binding site (RBS), a 6-His tag and restriction enzyme sites. pQE-9 is then digested with HindIII and EcoRI. The amplified sequences are ligated into pQE-9 and are inserted in frame with the sequence encoding for the histidine tag and the RBS. The ligation mixture is then used to transform E. coli strain M15/rep 4 (Qiagen, Inc.) by the procedure described in Sambrook, J. et al., Molecular Cloning: A Laboratory Manual, Cold Spring Laboratory Press, (1989). M15/rep4 contains multiple copies of the plasmid pREP4, which expresses the lacI repressor and also confers kanamycin resistance ($Kan^r$). Transformants are identified by their ability to grow on LB plates and ampicillin/kanamycin resistant colonies are selected. Plasmid DNA is isolated and confirmed by restriction analysis. Clones containing the desired constructs are grown overnight (O/N) in liquid culture in LB media supplemented with both Amp (100 ug/ml) and Kan (25 ug/ml). The O/N culture is used to inoculate a large culture at a ratio of 1:100 to 1:250. The cells are grown to an optical density 600 (O.D.$^{600}$) of between 0.4 and 0.6. IPTG ("Isopropyl-B-D-thiogalacto pyranoside") is then added to a final concentration of 1 mM. IPTG induces by inactivating the lacI repressor, clearing the P/O leading to increased gene expression. Cells are grown an extra 3 to 4 hours. Cells are then harvested by centrifugation. The cell pellet is solubilized in the chaotropic agent 6 Molar Guanidine HCl. After clarification, solubilized human amine receptor is purified from this solution by chromatography on a Nickel-Chelate column under conditions that allow for tight binding by proteins containing the 6-His tag (Hochuli, E. et al., J. Chromatography 411:177–184 (1984)). Human amine receptor protein is eluted from the column in 6 molar guanidine HCl pH 5.0 and for the purpose of renaturation adjusted to 3 molar guanidine HCl, 100 mM sodium phosphate, 10 mmolar glutathione (reduced) and 2 mmolar glutathione (oxidized). After incubation in this solution for 12 hours the protein is dialyzed to 10 mmolar sodium phosphate.

EXAMPLE 2

Cloning and expression of human amine receptor using the baculovirus expression system The DNA sequence encoding the full length human amine receptor protein, ATCC # 97181, is amplified using PCR oligonucleotide primers corresponding to the 5' and 3' sequences of the gene:

The 5' primer has the sequence 5' 5' CGGGATCCCTC-CATGAGA GCTGTCTTCATC 3' (SEQ ID No. 5) and contains a BamHI restriction enzyme site followed by 4 nucleotides resembling an efficient signal for the initiation of translation in eukaryotic cells (Kozak, M., J. Mol. Biol., 196:947–950 (1987) which is just behind the first 18 nucleotides of the human amine receptor gene.

The 3' primer has the sequence 5' CGGGATCCCGCT-CATTCTTGG TACAAATC 3' (SEQ ID No. 6) and contains the cleavage site for the restriction endonuclease BamHI and 18 nucleotides complementary to the 3' non-translated sequence of the human amine receptor gene. The amplified sequences are isolated from a 1% agarose gel using a commercially available kit ("Geneclean," BIO 101 Inc., La Jolla, Calif.). The fragment is then digested with the endonucleases BamHI and then purified again on a 1% agarose gel. This fragment is designated F2.

The vector pRG1 (modification of pVL941 vector, discussed below) is used for the expression of the human amine receptor protein using the baculovirus expression system (for review see: Summers, M. D. and Smith, G. E. 1987, A manual of methods for baculovirus vectors and insect cell culture procedures, Texas Agricultural Experimental Station Bulletin No. 1555). This expression vector contains the strong polyhedrin promoter of the *Autographa californica* nuclear polyhedrosis virus (AcMNPV) followed by the recognition sites for the restriction endonucleases BamHI. The polyadenylation site of the simian virus (SV)40 is used for efficient polyadenylation. For an easy selection of recombinant viruses the beta-galactosidase gene from *E.coli* is inserted in the same orientation as the polyhedrin promoter followed by the polyadenylation signal of the polyhedrin gene. The polyhedrin sequences are flanked at both sides by viral sequences for the cell-mediated homologous recombination of co-transfected wild-type viral DNA. Many other baculovirus vectors could be used in place of pRG1 such as pAc373, pVL941 and pAcIM1 (Luckow, V. A. and Summers, M. D., Virology, 170:31–39).

The plasmid is digested with the restriction enzymes BamHI and then dephosphorylated using calf intestinal phosphatase by procedures known in the art. The DNA is then isolated from a 1 agarose gel using the commercially available kit ("Geneclean" BIO 101 Inc., La Jolla, Calif.). This vector DNA is designated V2.

Fragment F2 and the dephosphorylated plasmid V2 are ligated with T4 DNA ligase. *E.coli* HB101 cells are then transformed and bacteria identified that contained the plasmid (pBac-Human amine receptor) with the human amine receptor gene using the enzyme BamHI. The sequence of the cloned fragment is confirmed by DNA sequencing.

5 μg of the plasmid pBac-Human amine receptor is co-transfected with 1.0 μg of a commercially available linearized baculovirus ("BaculoGold™ baculovirus DNA", Pharmingen, San Diego, Calif.) using the lipofection method (Felgner et al. Proc. Natl. Acad. Sci. USA, 84:7413–7417 (1987)).

1 μg of BaculoGold™ virus DNA and 5 μg of the plasmid pBac-Human amine receptor are mixed in a sterile well of a microtiter plate containing 50 μl of serum free Grace's medium (Life Technologies Inc., Gaithersburg, Md.). Afterwards 10 μl Lipofectin plus 90 μl Grace's medium are added, mixed and incubated for 15 minutes at room temperature. Then the transfection mixture is added dropwise to the Sf9 insect cells (ATCC CRL 1711) seeded in a 35 mm tissue culture plate with 1 ml Grace's medium without serum. The plate is rocked back and forth to mix the newly added solution. The plate is then incubated for 5 hours at 27° C. After 5 hours the transfection solution is removed from the plate and 1 ml of Grace's insect medium supplemented with 10% fetal calf serum is added. The plate is put back into an incubator and cultivation continued at 27° C. for four days.

After four days the supernatant is collected and a plaque assay performed similar as described by Summers and Smith (supra). As a modification an agarose gel with "Blue Gal" (Life Technologies Inc., Gaithersburg) is used which allows an easy isolation of blue stained plaques. (A detailed description of a "plaque assay" can also be found in the user's guide for insect cell culture and baculovirology distributed by Life Technologies Inc., Gaithersburg, page 9–10).

Four days after the serial dilution, the viruses are added to the cells and blue stained plaques are picked with the tip of an Eppendorf pipette. The agar containing the recombinant viruses is then resuspended in an Eppendorf tube containing 200 μl of Grace's medium. The agar is removed by a brief centrifugation and the supernatant containing the recombinant baculovirus is used to infect Sf9 cells seeded in 35 mm dishes. Four days later the supernatants of these culture dishes are harvested and then stored at 4° C.

Sf9 cells are grown in Grace's medium supplemented with 10% heat-inactivated FBS. The cells are infected with the recombinant baculovirus V-Human amine receptor at a multiplicity of infection (MOI) of 2. Six hours later the medium is removed and replaced with SF900 II medium minus methionine and cysteine (Life Technologies Inc., Gaithersburg). 42 hours later 5 μCi of $^{35}$S-methionine and 5 μCi $^{35}$S cysteine (Amersham) are added. The cells are further incubated for 16 hours before they are harvested by centrifugation and the labelled proteins visualized by SDS-PAGE and autoradiography.

EXAMPLE 3

Expression of Recombinant Human Amine Receptor in COS cells

The expression of plasmid, Human amine receptor HA is derived from a vector pcDNAI/Amp (Invitrogen) containing: 1) SV40 origin of replication, 2) ampicillin resistance gene, 3) *E.coli* replication origin, 4) CMV promoter followed by a polylinker region, a SV40 intron and polyadenylation site. A DNA fragment encoding the entire Human amine receptor precursor and a HA tag fused in frame to its 3' end is cloned into the polylinker region of the vector, therefore, the recombinant protein expression is directed under the CMV promoter. The HA tag correspond to an epitope derived from the influenza hemagglutinin protein as previously described (I. Wilson, et al., Cell, 37:767, (1984)). The infusion of HA tag to the target protein allows easy detection of the recombinant protein with an antibody that recognizes the HA epitope.

The plasmid construction strategy is described as follows: The DNA sequence encoding Human amine receptor, ATCC # 97181, is constructed by PCR using two primers: the 5' primer 5' GTCCAAGCTTGCCACCATGAGAGCT-GTCTTCATC 3' (SEQ ID No. 7) contains a HindIII site followed by 18 nucleotides of Human amine receptor coding sequence starting from the initiation codon; the 3' sequence 5' CTAGCTCGAGTCAAGCGTA GTCTGGGACGTCG-TATGGGTAGCATTCTTGGTACAAATCAAC 3' (SEQ ID No. 8) contains complementary sequences to an XhoI site, translation stop codon, HA tag and the last 18 nucleotides of the Human amine receptor coding sequence (not including the stop codon). Therefore, the PCR product contains a HindIII site, human amine receptor coding sequence followed by HA tag fused in frame, a translation termination stop codon next to the HA tag, and an HindIII site. The PCR amplified DNA fragment and the vector, pcDNAI/Amp, are digested with HindIII and XhoI restriction enzymes and ligated. The ligation mixture is transformed into *E. coli* strain SURE (Stratagene Cloning Systems, La Jolla, Calif.) the transformed culture is plated on ampicillin media plates and resistant colonies are selected. Plasmid DNA is isolated from transformants and examined by restriction analysis for the presence of the correct fragment. For expression of the recombinant amine receptor, COS cells are transfected with the expression vector by DEAEDEXTRAN method (J. Sambrook, E. Fritsch, T. Maniatis, Molecular Cloning: A Laboratory Manual, Cold Spring Laboratory Press, (1989)). The expression of the Human amine receptor HA protein is detected by radiolabelling and immunoprecipitation method (E. Harlow, D. Lane, Antibodies: A Laboratory Manual, Cold Spring Harbor Laboratory Press, (1988)). Cells are labelled for 8 hours with $^{35}$S-cysteine two days post transfection. Culture media is then collected and cells are lysed with detergent (RIPA buffer (150 mM NaCl, 1% NP-40, 0.1% SDS, 1% NP-40, 0.5% DOC, 50 mM Tris, pH 7.5) (Wilson, I. et al., Id. 37:767 (1984)). Both cell lysate and culture media are precipitated with a HA specific monoclonal antibody. Proteins precipitated are analyzed on 15% SDS-PAGE gels.

EXAMPLE 4

Expression pattern of Human amine receptor in human tissue

Northern blot analysis is carried out to examine the levels of expression of Human amine receptor in human tissues. Total cellular RNA samples are isolated with RNAzol™ B system (Biotecx Laboratories, Inc. Houston, Tex.). About 10 µg of total RNA isolated from each human tissue specified is separated on 1% agarose gel and blotted onto a nylon filter (Sambrook, Fritsch, and Maniatis, Molecular Cloning, Cold Spring Harbor Press, (1989)). The labeling reaction is done according to the Stratagene Prime-It kit with Song DNA fragment. The labeled DNA is purified with a Select-G-50 column (5 Prime - 3 Prime, Inc. Boulder, Colo.). The filter is then hybridized with radioactive labeled full length Human amine receptor gene at 1,000,000 cpm/ml in 0.5 M NaPO$_4$, pH 7.4 and 7% SDS overnight at 65° C. After wash twice at room temperature and twice at 60° C. with 0.5× SSC, 0.1% SDS, the filter is then exposed at −70° C. overnight with an intensifying screen.

EXAMPLE 5

Expression via Gene Therapy

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin, is added. This is then incubated at 37° C. for approximately one week. At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al, DNA, 7:219–25 (1988) flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention is amplified using PCR primers which correspond to the 5' and 3' end sequences respectively. The 5' primer contains an EcoRI site and the 3' primer contains a HindIII site. Equal quantities of the Moloney murine sarcoma virus linear backbone and the EcoRI and HindIII fragment are added together, in the presence of T4 DNA ligase. The resulting mixture is maintained under conditions appropriate for ligation of the two fragments. The ligation mixture is used to transform bacteria HB101, which are then plated onto agar-containing kanamycin for the purpose of confirming that the vector had the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells are transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product.

Numerous modifications and variations of the present invention are possible in light of the above teachings and, therefore, within the scope of the appended claims, the invention may be practiced otherwise than as particularly described.

What is claimed is:

1. A method for producing a polypeptide comprising the steps of:
   (I) expressing in a recombinant host cell a polynucleotide encoding a polypeptide having an amino acid sequence selected from the group consisting of:
      (a) amino acid 1 to 337 in SEQ ID NO:2; and
      (b) amino acid 2 to 337 in SEQ ID NO:2; and
   (II) recovering said expressed polypeptide.

2. The method of claim 1, wherein said amino acid sequence is (a).

3. The method of claim 2, wherein said polynucleotide has the sequence of nucleotides 252 to 1262 in SEQ ID NO:1.

4. The method of claim 1, wherein said amino acid sequence is (b).

5. The method of claim 4, wherein said polynucleotide has the sequence of nucleotides 255 to 1262 in SEQ ID NO:1.

6. An isolated polynucleotide selected from the group consisting of:
   (a) a polynucleotide encoding a polypeptide comprising amino acids 1 to 337 in SEQ ID NO:2;
   (b) a polynucleotide encoding a polypeptide comprising amino acids 2 to 337 in SEQ ID NO:2;
   (c) the complement of (a) or (b); and
   (d) a polynucleotide encoding a polypeptide comprising 30 contiguous amino acids of SEQ ID NO:2.

7. The isolated polynucleotide of claim 6, which is (a).

8. The isolated polynucleotide of claim 7, wherein said polynucleotide comprises nucleotides 252 to 1265 in SEQ ID NO:1.

9. The isolated polynucleotide of claim 7, wherein said polynucleotide comprises nucleotides 252 to 1262 in SEQ ID NO:1.

10. The isolated polynucleotide of claim 6, which is (b).

11. The isolated polynucleotide of claim 10, wherein said polynucleotide comprises nucleotides 255 to 1265 in SEQ ID NO:1.

12. The isolated polynucleotide of claim 10, wherein said polynucleotide comprises nucleotides 255 to 1262 in SEQ ID NO:1.

13. The isolated polynucleotide of claim 6, which is (c).

14. The isolated polynucleotide of claim 6, which is (d).

15. The isolated polynucleotide of claim 6, which is DNA.

16. The isolated polynucleotide of claim 6, which is RNA.

17. A method of making a recombinant vector comprising inserting the polynucleotide of claim 6 into a vector in operable linkage to a promoter.

18. A recombinant vector made by the method of claim 16.

19. A method of making a host cell comprising introducing the recombinant vector of claim 17 into a host cell.

20. A host cell made by the method of claim 18.

21. An isolated polynucleotide comprising nucleotides selected form the group consisting of:
   (a) 20 contiguous nucleotides of SEQ ID NO:1; and
   (b) the complement of (a).

22. The isolated polynucleotide of claims which is (a).

23. The isolated polynucleotide of claim 21, which is (b).

24. The isolated polynucleotide of claim 22, which comprises 30 contiguous nucleotides of SEQ ID NO:1.

25. The isolated polynucleotide of claim 22, which comprises 50 contiguous nucleotides of SEQ ID NO:1.

* * * * *

UNITED STATES PATENT AND TRADEMARK OFFICE
CERTIFICATE OF CORRECTION

PATENT NO. : 5,928,890
DATED : July 27, 1999
INVENTOR(S) : Li

It is certified that error appears in the above-identified patent and that said Letters Patent is hereby corrected as shown below:

Title page,
Line 1, of item [75] ("Inventor"), after "Gaithersburg,", please insert -- Steven M. Ruben, Olney, both of --.

Column 35,
Line 41, at claim 1, please delete "acid" and insert therein -- acids --.
Line 42, at claim 1, please delete "acid" and insert therein -- acids --.

Column 36,
Line 51, at claim 18, please delete "16" and insert therein -- 17 --.
Line 53, at claim 19, please delete "17" and insert therein -- 18 --.
Line 54, at claim 20, please delete "18" and insert therein -- 19 --.
Line 57, at claim 21, please delete "form" and insert therein -- from --.
Line 60, at claim 22, please delete "claims" and insert therein -- claim 21 --.
Line 64, at claim 25, please delete "22" and insert therein -- 24 --.

Signed and Sealed this

Fourth Day of September, 2001

Attest:

*Nicholas P. Godici*

NICHOLAS P. GODICI
*Attesting Officer*   *Acting Director of the United States Patent and Trademark Office*

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
      (A) LENGTH: 1380 base pairs
      (B) TYPE: nucleic acid
      (C) STRANDEDNESS: double
      (D) TOPOLOGY: linear (ii) MOLECULE TYPE: DNA (genomic)

(ix) FEATURE:
    (A) NAME/KEY: CDS
    (B) LOCATION: 252..1262

(xi) SEQUENCE DESCRIPTION: SEQ ID NO:1:

```
CTAGAGCTAG CAGGAGTAAC TCTCATGGAA CCTTGGAAAC CATTCTTCAA TTGAATTTCA        60

GGGCACATTT GAATCAGTAC CCAGGGGCAC TGTACTATGC TCCCAGCTGG ACCTTAGTTT       120

CCTCCTCCTC GTTTCACCCT GTGAGTAATT AACAGACAAA ATTTTTTTTT TTTTTTTTTT       180

TTTTTTTTTT TTTTTGCCCT CCAGTGGAGA AGGTGGCCAG TTCTCAGACA GAGGAAGAGT       240

AGAAATCATA A ATG AGA GCT GTC TTC ATC CAA GGT GCT GAA GAG CAC CCT        290
             Met Arg Ala Val Phe Ile Gln Gly Ala Glu Glu His Pro
               1               5                  10

GCG GCA TTC TGC TAC CAG GTG AAT GGG TCT TGC CCC AGG ACA GTA CAT         338
Ala Ala Phe Cys Tyr Gln Val Asn Gly Ser Cys Pro Arg Thr Val His
         15                  20                  25

ACT CTG GGC ATC CAG TTG GTC ATC TAC CTG ACC TGT GCA GCA GGC ATG         386
Thr Leu Gly Ile Gln Leu Val Ile Tyr Leu Thr Cys Ala Ala Gly Met
 30                  35                  40                  45

CTG ATT ATC GTG CTA GGG AAT GTA TTT GTG GCA TTT GCT GTG TCC TAC         434
Leu Ile Ile Val Leu Gly Asn Val Phe Val Ala Phe Ala Val Ser Tyr
                 50                  55                  60

TTC AAA GCG CTT CAC ACG CCC ACC AAC TTC CTG CTG CTC TCC CTG GCC         482
Phe Lys Ala Leu His Thr Pro Thr Asn Phe Leu Leu Leu Ser Leu Ala
                     65                  70                  75

CTG GCT GAC ATG TTT CTG GGT CTG CTG GTG CTG CCC CTC AGC ACC ATT         530
Leu Ala Asp Met Phe Leu Gly Leu Leu Val Leu Pro Leu Ser Thr Ile
             80                  85                  90

CGC TCA GTG GAG AGC TGC TGG TTC TTC GGG GAC TTC CTC TGC CGC CTG         578
Arg Ser Val Glu Ser Cys Trp Phe Phe Gly Asp Phe Leu Cys Arg Leu
     95                 100                 105

CAC ACC TAC CTG GAC ACC CTC TTC TGC CTC ACC TCC ATC TTC CAT CTC         626
His Thr Tyr Leu Asp Thr Leu Phe Cys Leu Thr Ser Ile Phe His Leu
110                 115                 120                 125

TGT TTC ATT TCC ATT GAC CGC CAC TGT GCC ATC TGT GAC CCC CTG CTC         674
Cys Phe Ile Ser Ile Asp Arg His Cys Ala Ile Cys Asp Pro Leu Leu
                130                 135                 140

TAT CCC TCC AAG TTC ACA GTG AGG GTG GCT CTC AGG TAC ATC CTG GCA         722
Tyr Pro Ser Lys Phe Thr Val Arg Val Ala Leu Arg Tyr Ile Leu Ala
                    145                 150                 155

GGA TGG GGG GTG CCC GCA GCA TAC ACT TCG TTA TTC CTC TAC ACA GAT         770
Gly Trp Gly Val Pro Ala Ala Tyr Thr Ser Leu Phe Leu Tyr Thr Asp
            160                 165                 170

GTG GTA GAG ACA AGG CTC AGC CAG TGG CTG GAA GAG ATG CCT TGT GTG         818
Val Val Glu Thr Arg Leu Ser Gln Trp Leu Glu Glu Met Pro Cys Val
175                 180                 185

GGC AGT TGC CAG CTG CTG CTC AAT AAA TTT TGG GGC TGG TTA AAC TTC         866
Gly Ser Cys Gln Leu Leu Leu Asn Lys Phe Trp Gly Trp Leu Asn Phe
190                 195                 200                 205

CCT TTG TTC TTT GTC CCC TGC CTC ATT ATG ATC AGC TTG TAT GTG AAG         914
Pro Leu Phe Phe Val Pro Cys Leu Ile Met Ile Ser Leu Tyr Val Lys
                210                 215                 220

ATC TTT GTG GTT GCT ACC AGA CAG GCT CAG CAG ATT ACC ACA TTG AGC         962
Ile Phe Val Val Ala Thr Arg Gln Ala Gln Gln Ile Thr Thr Leu Ser
                    225                 230                 235

AAA AGC CTG GCT GGG GCT GCC AAG CAT GAG AGA AAA GCT GCC AAG ACC        1010
Lys Ser Leu Ala Gly Ala Ala Lys His Glu Arg Lys Ala Ala Lys Thr
                240                 245                 250

CTG GGC ATT GTT GTG GGC ATA TAC CTC TTG TGC TGG CTG CCC TTC ACC        1058
```

```
Leu Gly Ile Val Val Gly Ile Tyr Leu Leu Cys Trp Leu Pro Phe Thr
    255                 260                 265

ATA GAC ACG ATG GTC GAC AGC CTC CTT CAC TTT ATC ACA CCC CCA CTG      1106
Ile Asp Thr Met Val Asp Ser Leu Leu His Phe Ile Thr Pro Pro Leu
270             275                 280                 285

GTC TTT GAC ATC TTT ATC TGG TTT GCT TAC TTC AAC TCA GCC TGC AAC      1154
Val Phe Asp Ile Phe Ile Trp Phe Ala Tyr Phe Asn Ser Ala Cys Asn
                290                 295                 300

CCC ATC ATC TAT GTC TTT TCC TAC CAG TGG TTT CGG AAG GCA CTG AAA      1202
Pro Ile Ile Tyr Val Phe Ser Tyr Gln Trp Phe Arg Lys Ala Leu Lys
                305                 310                 315

CTC ACA CTG AGC CAG AAG GTC TTC TCA CCG CAG ACA CGC ACT GTT GAT      1250
Leu Thr Leu Ser Gln Lys Val Phe Ser Pro Gln Thr Arg Thr Val Asp
            320                 325                 330

TTG TAC CAA GAA TGATTCCTTC TACTAAATGC AGGCAAGGAG TAGGACCTCA          1302
Leu Tyr Gln Glu
    335

CAGGAAAGAT AAGTGGCACT GTGACCGCGG GCTGTGTGGT GTTGAGTTTG TGGGCATGCT    1362

TCCAGGACAG CATGGGTT                                                  1380

(2) INFORMATION FOR SEQ ID NO:2:

(i) SEQUENCE CHARACTERISTICS:
        (A) LENGTH: 337 amino acids
        (B) TYPE: amino acid
        (D) TOPOLOGY: linear (ii) MOLECULE TYPE: protein (xi) SEQUENCE DESCRIPTION: SEQ ID NO:2:

Met Arg Ala Val Phe Ile Gln Gly Ala Glu Glu His Pro Ala Ala Phe
1               5                   10                  15

Cys Tyr Gln Val Asn Gly Ser Cys Pro Arg Thr Val His Thr Leu Gly
                20                  25                  30

Ile Gln Leu Val Ile Tyr Leu Thr Cys Ala Ala Gly Met Leu Ile Ile
            35                  40                  45

Val Leu Gly Asn Val Phe Val Ala Phe Ala Val Ser Tyr Phe Lys Ala
        50                  55                  60

Leu His Thr Pro Thr Asn Phe Leu Leu Leu Ser Leu Ala Leu Ala Asp
65                  70                  75                  80

Met Phe Leu Gly Leu Leu Val Leu Pro Leu Ser Thr Ile Arg Ser Val
                85                  90                  95

Glu Ser Cys Trp Phe Phe Gly Asp Phe Leu Cys Arg Leu His Thr Tyr
                100                 105                 110

Leu Asp Thr Leu Phe Cys Leu Thr Ser Ile Phe His Leu Cys Phe Ile
            115                 120                 125

Ser Ile Asp Arg His Cys Ala Ile Cys Asp Pro Leu Leu Tyr Pro Ser
        130                 135                 140

Lys Phe Thr Val Arg Val Ala Leu Arg Tyr Ile Leu Ala Gly Trp Gly
145                 150                 155                 160

Val Pro Ala Ala Tyr Thr Ser Leu Phe Leu Tyr Thr Asp Val Val Glu
                165                 170                 175

Thr Arg Leu Ser Gln Trp Leu Glu Glu Met Pro Cys Val Gly Ser Cys
            180                 185                 190

Gln Leu Leu Leu Asn Lys Phe Trp Gly Trp Leu Asn Phe Pro Leu Phe
        195                 200                 205

Phe Val Pro Cys Leu Ile Met Ile Ser Leu Tyr Val Lys Ile Phe Val
210                 215                 220
```

```
Val Ala Thr Arg Gln Ala Gln Gln Ile Thr Thr Leu Ser Lys Ser Leu
225                 230                 235                 240

Ala Gly Ala Ala Lys His Glu Arg Lys Ala Ala Lys Thr Leu Gly Ile
                245                 250                 255

Val Val Gly Ile Tyr Leu Leu Cys Trp Leu Pro Phe Thr Ile Asp Thr
                260                 265                 270

Met Val Asp Ser Leu Leu His Phe Ile Thr Pro Pro Leu Val Phe Asp
                275                 280                 285

Ile Phe Ile Trp Phe Ala Tyr Phe Asn Ser Ala Cys Asn Pro Ile Ile
                290                 295                 300

Tyr Val Phe Ser Tyr Gln Trp Phe Arg Lys Ala Leu Lys Leu Thr Leu
305                 310                 315                 320

Ser Gln Lys Val Phe Ser Pro Gln Thr Arg Thr Val Asp Leu Tyr Gln
                325                 330                 335

Glu
```

(2) INFORMATION FOR SEQ ID NO:3:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

CGGAATTCCT UATGAGAGCT GTCTTCATC                        29

(2) INFORMATION FOR SEQ ID NO:4:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

CGGAAGCTTC GTCATTCTTG GTACAAATCA AC                   32

(2) INFORMATION FOR SEQ ID NO:5:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

CGGGATCCCT CCATGAGAGC TGTCTTCATC                       30

(2) INFORMATION FOR SEQ ID NO:6:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

CGGGATCCCG CTCATTCTTG GTACAAATC                                                      29

(2) INFORMATION FOR SEQ ID NO:7:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

GTCCAAGCTT GCCACCATGA GAGCTGTCTT CATC                                                34

(2) INFORMATION FOR SEQ ID NO:8:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

CTAGCTCGAG TCAAGCGTAG TCTGGGACGT CGTATGGGTA GCATTCTTGG TACAAATCAA                    60

C                                                                                   61

(2) INFORMATION FOR SEQ ID NO:9:

(i) SEQUENCE CHARACTERISTICS:
        (A) LENGTH: 365 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:9:

```
Ala Arg Leu Leu Val Leu Ala Ser Pro Pro Ala Ser Leu Leu Pro Pro
1               5                   10                  15

Ala Ser Glu Gly Ser Ala Pro Leu Ser Gln Gln Trp Thr Ala Gly Met
            20                  25                  30

Gly Leu Leu Val Ala Leu Ile Val Leu Leu Ile Val Val Gly Asn Val
        35                  40                  45

Leu Val Ile Val Ala Ile Ala Lys Thr Pro Arg Leu Gln Thr Leu Thr
    50                  55                  60

Asn Leu Phe Ile Met Ser Leu Ala Ser Ala Asp Leu Val Met Gly Leu
65                  70                  75                  80

Leu Val Val Pro Phe Gly Ala Thr Ile Val Val Trp Gly Arg Trp Glu
                85                  90                  95

Tyr Gly Ser Phe Phe Cys Glu Leu Trp Thr Ser Val Asp Val Leu Cys
            100                 105                 110

Val Thr Ala Ser Ile Glu Thr Leu Cys Val Ile Ala Leu Asp Arg Tyr
        115                 120                 125

Leu Ala Ile Thr Ser Pro Phe Arg Tyr Gln Ser Leu Leu Thr Arg Ala
    130                 135                 140

Arg Ala Arg Ala Leu Val Cys Thr Val Trp Ala Ile Ser Ala Leu Val
145                 150                 155                 160

Ser Phe Leu Pro Ile Leu Met His Trp Trp Arg Ala Glu Ser Asp Glu
```

```
            165                 170                 175
Ala Arg Arg Cys Tyr Asn Asp Pro Lys Cys Cys Asp Phe Val Thr Asn
            180                 185                 190

Arg Ala Tyr Ala Ile Ala Ser Ser Val Val Ser Phe Tyr Val Pro Leu
            195                 200                 205

Cys Ile Met Ala Phe Val Tyr Leu Arg Val Phe Arg Glu Ala Gln Lys
            210                 215                 220

Gln Val Lys Lys Ile Asp Ser Cys Glu Arg Arg Phe Leu Gly Gly Pro
225                 230                 235                 240

Ala Arg Pro Pro Ser Pro Glu Pro Ser Pro Ser Pro Gly Pro Pro Arg
            245                 250                 255

Pro Ala Asp Ser Leu Ala Asn Gly Arg Ser Ser Lys Arg Arg Pro Ser
            260                 265                 270

Arg Leu Val Ala Leu Arg Glu Gln Lys Ala Leu Lys Thr Leu Gly Ile
            275                 280                 285

Ile Met Gly Val Phe Thr Leu Cys Trp Leu Pro Phe Phe Leu Ala Asn
            290                 295                 300

Val Val Lys Ala Phe His Arg Asp Leu Val Pro Asp Arg Leu Phe Val
305                 310                 315                 320

Phe Phe Asn Trp Leu Gly Tyr Ala Asn Ser Ala Phe Asn Pro Ile Ile
            325                 330                 335

Tyr Cys Arg Ser Pro Asp Phe Arg Lys Ala Phe Gln Arg Leu Leu Cys
            340                 345                 350

Cys Ala Arg Arg Ala Ala Cys Arg Arg Arg Ala Ala His
            355                 360                 365

(2) INFORMATION FOR SEQ ID NO:10:

(i) SEQUENCE CHARACTERISTICS:
         (A) LENGTH: 353 amino acids
         (B) TYPE: amino acid
         (C) STRANDEDNESS: Not Relevant
         (D) TOPOLOGY: linear (ii) MOLECULE TYPE: protein (xi) SEQUENCE DESCRIPTION: SEQ ID NO:10:

Asp Asp Asp Leu Glu Arg Gln Asn Trp Ser Arg Pro Phe Asn Gly Ser
1               5                   10                  15

Asp Gly Lys Ala Asp Arg Pro His Tyr Asn Tyr Tyr Ala Thr Leu Leu
            20                  25                  30

Thr Leu Leu Ile Ala Val Ile Val Phe Gly Asn Val Leu Val Cys Met
            35                  40                  45

Ala Val Ser Arg Glu Lys Ala Leu Gln Thr Thr Thr Asn Tyr Leu Ile
            50                  55                  60

Val Ser Leu Ala Val Ala Asp Leu Leu Val Ala Thr Leu Val Met Pro
65                  70                  75                  80

Trp Val Val Tyr Leu Glu Val Val Gly Glu Trp Lys Phe Ser Arg Ile
            85                  90                  95

His Cys Asp Ile Phe Val Thr Leu Asp Val Met Met Cys Thr Ala Ser
            100                 105                 110

Ile Leu Asn Leu Cys Ala Ile Ser Ile Asp Arg Tyr Thr Ala Val Ala
            115                 120                 125

Met Pro Met Leu Tyr Asn Thr Arg Tyr Ser Ser Lys Arg Arg Val Thr
            130                 135                 140

Val Met Ile Ser Ile Val Trp Val Leu Ser Phe Thr Ile Ser Cys Pro
145                 150                 155                 160
```

```
Leu Leu Phe Gly Leu Asn Asn Ala Asp Gln Asn Glu Cys Ile Ile Ala
            165                 170                 175

Asn Pro Ala Phe Val Val Tyr Ser Ser Ile Val Ser Phe Tyr Val Pro
            180                 185                 190

Phe Ile Val Thr Leu Leu Val Tyr Ile Lys Ile Tyr Ile Val Leu Arg
        195                 200                 205

Arg Arg Arg Lys Arg Val Asn Thr Lys Arg Ser Ser Arg Ala Phe Arg
        210                 215                 220

Ala His Leu Arg Ala Pro Leu Lys Glu Ala Ala Arg Arg Glu Lys Asn
225                 230                 235                 240

Gly His Ala Lys Asp His Pro Lys Ile Ala Lys Ile Phe Glu Ile Gln
                245                 250                 255

Thr Met Pro Asn Gly Lys Thr Arg Thr Ser Leu Lys Thr Met Ser Arg
            260                 265                 270

Arg Lys Leu Ser Gln Gln Lys Glu Lys Lys Ala Thr Gln Met Leu Ala
            275                 280                 285

Ile Val Leu Gly Val Phe Ile Ile Cys Trp Leu Pro Phe Phe Ile Thr
        290                 295                 300

His Ile Leu Asn Ile His Cys Asp Cys Asn Ile Pro Pro Val Leu Tyr
305                 310                 315                 320

Ser Ala Phe Thr Trp Leu Gly Tyr Val Asn Ser Ala Val Asn Pro Ile
                325                 330                 335

Ile Tyr Thr Thr Phe Asn Ile Glu Phe Arg Lys Ala Phe Leu Lys Ile
            340                 345                 350

Leu
```